United States Patent [19]

MacPhee et al.

[11] 4,221,782
[45] Sep. 9, 1980

[54] FISH CULTURE BY STICKLEBACK POPULATION ERADICATION

[75] Inventors: Craig MacPhee, Moscow, Id.; Fred F. Cheng, Taipei, Taiwan

[73] Assignee: Idaho Research Foundation, Inc., Moscow, Id.

[21] Appl. No.: 893,061

[22] Filed: Apr. 3, 1978

[51] Int. Cl.$^3$ .................... A01N 47/08; A01N 55/00; A01N 59/00
[52] U.S. Cl. ........................................ 424/127; 119/3; 424/131; 424/150; 424/153; 424/154; 424/184; 424/226; 424/DIG. 9
[58] Field of Search ............... 424/127, 153, 184, 154, 424/DIG. 9

[56] References Cited

U.S. PATENT DOCUMENTS

| | | | |
|---|---|---|---|
| 3,389,685 | 6/1968 | MacPhee et al. | 424/343 |
| 4,132,780 | 1/1979 | McConnell | 424/154 |

OTHER PUBLICATIONS

Gregory, "Uses & Applications of Chemicals & Related Materials," (1939), p. 130.

*Primary Examiner*—Leonard Schenkman
*Attorney, Agent, or Firm*—Wells, St. John & Roberts

[57] ABSTRACT

Control of stickleback in streams and other locales is achieved by selective addition of chemicals that form free azide radicals in water, specifically sodium azide and potassium azide. Subsequent deactivation, when desired, is achieved by addition of calcium compounds. High selectively to stickleback can be achieved with minimal risk to desirable game fish in the salmon and trout groups.

9 Claims, No Drawings

FISH CULTURE BY STICKLEBACK POPULATION ERADICATION

BACKGROUND OF THE INVENTION

This invention concerns the improvement of fish culture through control of stickleback by treating its aquatic habitats with chemicals that contain the azide radical ($N_3-$) and dissociate to form free azide radicals in water. An example of one such chemical is sodium azide ($NaN_3$).

The selective eradication of pest fish allows more food for the desirable species. This permits the desirable fishes to grow faster and become less vulnerable to predation. Depensatory mortality of stickleback by unharmed desirable predators slows re-infestation of stickleback. Selective eradication does not destroy the gene pools of indigenous stocks of desirable fishes that are very difficult to replace.

On the other hand, the use of general toxicants kills both desirable and pest species of fish. After poisoning all species, stickleback populations would grow faster than salmonid populations and thus gain the advantage in competition for food. The stickleback population would grow faster due to shorter generation time and lack of predators. Native stocks of salmonids would be destroyed and difficult to re-establish.

The stickleback, or target fish, and a salmonid, a desirable fish, were exposed together to low concentrations of single toxicants in 24-hour bioassays at 15 degrees Celsius. The order and time of death of each species of fish were noted. The results this procedure indicated that azides are extremely selective for stickleback and harmless to salmonids.

Five species of the stickleback family exist in North America of which the threespine stickleback (*Gasterosteus aculeatus*) is the most notorious pest. The threespine stickleback is almost circumpolar in distribution and is normally found in marine, brackish and fresh waters of the northern hemisphere.

The stickleback has a high reproductive potential; as many as 600 eggs have been found in one nest. The fact that the male guards the nest and newly hatched young enhances juvenile survival. The stickleback has the advantage of a much shorter generation time (one to two years) than most salmon and trout (two to seven years). This permits the stickleback to increase their numbers at a faster rate than salmonids and become extremely abundant. Furthermore, stickleback have an exceptionally high rate of survival since they take advantage of inshore areas in which large predators are not commonly found.

Stickleback greatly reduces the populations of food and game fishes, usually species of salmon and trout, with which they compete. Furthermore, it is a successful competitor for limited food supplies and attacks juvenile salmon and trout. The result is that trout and salmon are scarce where stickleback populations abound. As stickleback have no value as a sport or commercial fish, they are considered a pest fish and constitute an aggravating problem wherever they exist with desirable species of fish.

Spot poisoning of stickleback with general toxicants like rotenone and toxaphene has been ineffective in controlling stickleback numbers since any benefits are very temporary and such methods are often carried out at the expense of killing natural stocks of desirable species.

We have found that azide compounds are outstanding toxicants to stickleback in dilutions which are harmless to desirable aquatic species.

DESCRIPTION OF THE INVENTION

The following examples are illustrative of the invention:

The laboratory facilities that were used consisted primary of four vats (120 cm long × 90 cm wide × 90 cm deep) for fish storage and acclimation purposes and four water baths or fish assay tables (3.5 m long × 0.6 m wide and 0.36 m deep). The water temperature of each vat and table was individually controlled. Each fish assay table controlled the temperature of a battery of twenty identical vessels in which static assays were conducted. Some bioassays were made in constant temperature controlled rooms.

The fishes were conditioned and tested at the average Celsius temperature indicated in the tables of the examples. These temperatures were accurate to within one degree. The conditioning period varied between one to ten days. The test fishes were transferred to 19.6-liter assay aquaria and starved for 24 hours before a chemical was added. Each aquarium contained 15 liters of water which was aerated by means of a single stone airbreaker. Five fish per vessel was the common number tested. The load (grams of fish per liter of water) varied as indicated in the examples.

Control fish were conditioned in the same manner as the test fish, but no chemical was added to the control vessels during the assays. The control data are the first concentration (0.0) reported in the tables.

Delineation bioassays determined primarily the $LC_{50}$ and $LC_{100}$ of stickleback and the $LC_0$ and $LC_{50}$ of salmonids. The selectivity index $LC_{50}/LC_{50}$ compares the lethal concentrations that cause 50% mortalities for each species. The safety index $LC_0/LC_{100}$ compares the maximum concentration that kills zero percent of a preferred species with the minimum concentration that kills 100% of a target species.

The desirable fishes tested in bioassays included the sockeye salmon (*Oncorhynchus nerka*), chinook salmon, (*O. tschawytscha*) and the steelhead, a sea-run variety of rainbow trout (*Salmo gairdneri*).

For bioassay purposes the length of fish is given as fork length and fish are measured in millimeters.

EXAMPLE 1 (Exploratory Assays)

Stickleback (mean length, 36 mm) and steelhead (mean length, 68 mm) were treated with various concentrations of potassium azide in laboratory facilities for 72 hours at 10 degrees Celsius. to determine approximate selectivity and safety indices. The average bioassay load was 0.6 g/l for stickleback and 1.9 g/l for steelhead. The results of this experiment are tabulated in Table 1.

Table 1.

A comparison of percentage mortalities of the threespine stickleback and steelhead in artesian well water exposed to selected concentrations of potassium azide in 72-hour bioassays (10 fish per concentration) at a temperature of 10° C.

| Concentration mg/l | Elapsed time, hours | | | | |
|---|---|---|---|---|---|
| | 12 | 24 | 36 | 48 | 72 |
| 0.0 | 0 | 0 | 0 | 0 | 0 |
| 2.0 | 90 | 100 | 100 | 100 | 100 |
| 3.0 | 100 | 100 | 100 | 100 | 100 |

Table 1.-continued

A comparison of percentage mortalities of the three-
spine stickleback and steelhead in artesian well water exposed
to selected concentrations of potassium azide in 72-hour
bioassays (10 fish per concentration) at a temperature of 10° C.

| | Concentration mg/l | Elapsed time, hours | | | | |
|---|---|---|---|---|---|---|
| | | 12 | 24 | 36 | 48 | 72 |
| Stickleback | 4.5 | 100 | 100 | 100 | 100 | 100 |
| | 7.0 | 100 | 100 | 100 | 100 | 100 |
| | 10.0 | 100 | 100 | 100 | 100 | 100 |
| | 0.0 | 0 | 0 | 0 | 0 | 0 |
| | 4.5 | 0 | 0 | 0 | 0 | 0 |
| Steelhead | 10.0 | 0 | 0 | 0 | 0 | 20 |
| | 14.0 | 0 | 10 | 30 | 50 | 100 |
| | 20.0 | 0 | 40 | 100 | 100 | 100 |
| Selectivity index $LC_{50}/LC_{50}$ | | 10 | 10 | 7 | 7 | 5 |
| Safety index $LC_0/LC_{100}$ | | 7 | 5 | 5 | 5 | 2 |

Table 1 shows that in a 72-hour assay at 10 degrees Celsius using artesian well water, a 100% mortality of stickleback was achieved at a concentration of 2 mg/l of potassium azide; no mortality occurred in steelhead at concentrations below 4.5 mg/l.

The selectivity indices of stickleback and steelhead decreased from 10 to 5 and the safety indices decreased from 7 to 2 during a 72-hour exposure period. However, this decrease is an experimental artifact because 100% mortality of stickleback could have occurred if tested at concentrations of less than 2.0 mg/l in 72 and possibly 48 hours.

These bioassays substantiated our preliminary findings that potassium azide is selectively lethal to stickleback at concentrations nonlethal to steelhead.

EXAMPLE 2 (Temperature Delineations)

Stickleback (mean length, 44 mm) and sockeye (mean length, 74 mm) in artesian well water were treated with various concentrations of potassium azide in laboratory facilities for 96 hours at 5, 10 and 15 degrees Celsius to determine approximate selectivity and safety indices. The average bioassay load was 0.6 g/l for stickleback and 2.9 g/l for sockeye. the results of this experiment are tabulated in Tables 2 and 3.

Table 2.

A comparison of percentage mortalities of threespine stickleback and sockeye in artesian well water exposed to selected concentrations of potassium azide in 96-hour bioassays (20 fish per concentration) at temperatures of 5, 10 and 15 C.

| Temperature, degrees Centigrade | Species (length/range) | Concentration mg/l | Elapsed time, hours | | | | | |
|---|---|---|---|---|---|---|---|---|
| | | | 12 | 24 | 36 | 48 | 72 | 96 |
| 5 | Stickleback (21-61 mm) | 0.0 | 0 | 0 | 0 | 0 | 0 | 0 |
| | | 0.5 | 0 | 15 | 20 | 35 | 35 | 45 |
| | | 0.7 | 0 | 5 | 10 | 10 | 20 | 25 |
| | | 1.0 | 20 | 20 | 25 | 40 | 60 | 75 |
| | | 2.0 | 45 | 70 | 80 | 95 | 100 | 100 |
| | | 4.0 | 40 | 60 | 90 | 100 | 100 | 100 |
| | | 5.0 | 40 | 100 | 100 | 100 | 100 | 100 |
| | Sockeye (52-89 mm) | 0.0 | 0 | 0 | 0 | 0 | 0 | 0 |
| | | 5.0 | 0 | 0 | 0 | 0 | 0 | 20 |
| | | 7.0 | 0 | 0 | 0 | 0 | 10 | 35 |
| | | 10.0 | 0 | 0 | 0 | 10 | 60 | 75 |
| | | 13.0 | 0 | 5 | 45 | 50 | 95 | 95 |
| | | 16.0 | 45 | 70 | 80 | 95 | 100 | 100 |
| | | 20.0 | 85 | 100 | 100 | 100 | 100 | 100 |
| | | 23.0 | 100 | 100 | 100 | 100 | 100 | 100 |
| 10 | Stickleback (24-62 mm) | 0.0 | 0 | 0 | 0 | 0 | 0 | 0 |
| | | 0.7 | 0 | 0 | 0 | 0 | 0 | 25 |
| | | 1.0 | 5 | 15 | 25 | 55 | 55 | 70 |
| | | 2.0 | 15 | 25 | 75 | 95 | 95 | 100 |
| | | 3.0 | 35 | 75 | 100 | 100 | 100 | 100 |
| | | 4.0 | 70 | 90 | 100 | 100 | 100 | 100 |
| | | 5.0 | 60 | 100 | 100 | 100 | 100 | 100 |
| | | 6.0 | 100 | 100 | 100 | 100 | 100 | 100 |
| | Sockeye (58-92 mm) | 0.0 | 0 | 0 | 0 | 0 | 0 | 0 |
| | | 5.0 | 0 | 0 | 0 | 0 | 0 | 0 |
| | | 6.0 | 0 | 0 | 0 | 0 | 0 | 0 |
| | | 7.0 | 0 | 0 | 0 | 0 | 0 | 10 |
| | | 10.0 | 0 | 0 | 0 | 25 | 60 | 85 |
| | | 13.0 | 0 | 0 | 50 | 65 | 85 | 95 |
| | | 16.0 | 0 | 50 | 90 | 95 | 95 | 100 |
| | | 20.0 | 20 | 40 | 40 | 100 | 100 | 100 |
| 15 | Stickleback (23-75 mm) | 0.0 | 0 | 0 | 0 | 0 | 0 | 0 |
| | | 1.0 | 0 | 25 | 25 | 45 | 65 | 85 |
| | | 2.0 | 15 | 55 | 80 | 90 | 100 | 100 |
| | | 2.5 | 30 | 95 | 95 | 95 | 100 | 100 |
| | | 3.0 | 40 | 90 | 95 | 95 | 95 | 100 |
| | | 5.0 | 90 | 100 | 100 | 100 | 100 | 100 |
| | | 7.0 | 100 | 100 | 100 | 100 | 100 | 100 |
| | Sockeye (59-94 mm) | 0.0 | 0 | 0 | 0 | 0 | 0 | 0 |
| | | 3.0 | 0 | 0 | 0 | 0 | 0 | 0 |
| | | 4.0 | 0 | 0 | 0 | 0 | 0 | 0 |
| | | 5.0 | 0 | 0 | 0 | 0 | 0 | 35 |
| | | 7.0 | 0 | 0 | 0 | 0 | 35 | 85 |
| | | 10.0 | 0 | 0 | 10 | 35 | 55 | 90 |
| | | 13.0 | 0 | 15 | 85 | 90 | 95 | 95 |

Table 2.-continued

A comparison of percentage mortalities of threespine stickleback and sockeye in artesian well water exposed to selected concentrations of potassium azide in 96-hour bioassays (20 fish per concentration) at temperatures of 5, 10 and 15 C.

| Temperature, degrees Centigrade | Species (length/range) | Concentration mg/l | Elapsed time, hours | | | | | |
|---|---|---|---|---|---|---|---|---|
| | | | 12 | 24 | 36 | 48 | 72 | 96 |
| | | 16.0 | 10 | 75 | 09 | 95 | 100 | 100 |
| | | 20.0 | 50 | 100 | 100 | 100 | 100 | 100 |

Table 3.

Approximate selectivity and safety indices for the threespine stickleback and sockeye salmon assayed in artesian well water.

| Temperature, degrees Celcius | Index | Elapsed time, hours | | | | Mean index |
|---|---|---|---|---|---|---|
| | | 12 | 24 | 48 | 96 | |
| 5 | Selectivity | 8 | 8 | 10 | 10 | 9 |
| | Safety | 2 | 2 | 2 | 2 | 2 |
| 10 | Selectivity | 7 | 6 | 11 | 9 | 8 |
| | Safety | 3 | 3 | 2 | 3 | 3 |
| 15 | Selectivity | 7 | 7 | 10 | 7 | 8 |
| | Safety | 2 | 2 | 1 | 2 | 2 |

Table 2 shows that in artesian well water in a 96-hour assay at 5, 10, and 15 degrees Celsius a 100% mortality of stickleback was achieved at a concentration of 2 mg/l of potassium azide; no mortality occurred in sockeye at concentrations of 6 mg/l at 10 degrees Celsius and 4 mg/l at 15 degrees Celsius.

Extrapolation of the 5 degrees Celsius data suggests that no mortalities of sockeye would occur at 4 mg/l. Temperatures between 5 and 15 C did not markedly alter the toxicity and selectivity of potassium azide.

Table 3 indicates that the mean selectivity index as calculated from the 12-, 24-, 48- and 96-hour observations (a logarithmic progression) was about 8 and the mean safety index was about 2.

This series of experiments showed marked increase in the toxicity of potassium azide with increases in temperature.

EXAMPLE 3 (Comparison of Potassium and Sodium salts)

The equivalence of lethal concentrations of sodium and potassium azide was verified by timing the death of fingerling sockeye (length range, 58–94 mm) exposed to equivalent concentrations of the chemicals in artesian well water. The results of this experiment are tabulated in Table 4.

Table 4.

A comparison of equivalent lethal concentrations of potassium azide and sodium azide on the survival of sockeye tested in artesian well water (10 fish per concentration; load, 2.9 g/l).

| Chemical | Temperature, C. | Concentration mg/l | Death time of 10 fish, hours Range | Mean |
|---|---|---|---|---|
| Potassium Azide | 5 | 20 | 3–23 | 5.7 |
| Sodium Azide | 5 | 16* | 3–14 | 5.1 |
| Potassium Azide | 15 | 16 | 9–35 | 19.5 |
| Sodium Azide | 15 | 13** | 11–29 | 20.7 |

*equivalent to 20 mg/l Potassium Azide
**equivalent to 16 mg/l Potassium Azide

Table 4 shows that about 80 percent by weight of sodium azide as opposed to potassium azide is required in bioassays to achieve the same lethal concentrations. The value 0.8 represents the ratio of the equivalent weight of sodium azide, 65, divided by that of potassium azide, 81.

The data indicate that about equal equivalents of potassium or sodium azide give about equal mean times of death.

In this case concentrations of azides were purposely used that would cause death in a reasonably short period of time. Other bioassays show that temperature was not a significant factor in this experiment. The data suggest that only 80% by weight of sodium azide as opposed to potassium azide would be required in field applications to achieve the same results.

EXAMPLE 4 (Application to river conditions)

Mortality tests have shown that the $LC_{100}$ of stickleback in river water was 0.34 mg/l of sodium azide in 96-hour bioassays at 15 degrees Celsius. The $LC_{100}$ of stickleback in artesian well water was 2.00 mg/l under similar experimental conditions. Allowing for the 0.8 differential between sodium azide and potassium azide, sodium azide proved about 5 times more toxic to fish in river water that had relatively small amounts of dissolved solids as opposed to artesian water that had relatively large amounts of dissolved solids. The difference in the water quality of artesian and river water did not affect the selectivity of the azide, but the safety index of river water was about that of artesian water at 15 degrees Celsius.

Further experiments have shown that the $LC_0$ of chinook in sodium azide and artesian well water in 96-hour bioassays was 10.0 mg/l at 5° C. and 8.0 mg/l at 10° C. and 15° C.

The $LC_{100}$ for stickleback was obtained with potassium azide (Table 2). A correction factor of 0.8 was used to convert the $LC_{50}$ and $LC_{100}$ of potassium azide from Table 2 to those of sodium azide (Table 5). This procedure compensated for differences in molecular weights of the salts to obtain equivalent concentrations of the azide radical.

Table 5.

The $LC_{50}$ and $LC_{100}$ of stickleback in artesian well water exposed to potassium azide (the values were obtained from Table 2) and the calculated equivalents of sodium azide (concentrations of potassium azide multiplied by 0.8).

| Tempera- ture, C. | Azido salt | Elapsed time, hours | | | | | | | |
|---|---|---|---|---|---|---|---|---|---|
| | | 12 | | 24 | | 48 | | 96 | |
| | | $LC_{50}$ | $LC_{100}$ | $LC_{50}$ | $LC_{100}$ | $LC_{50}$ | $LC_{100}$ | $LC_{50}$ | $LC_{100}$ |
| 5 | K | 2.0 | 7.0 | 1.5 | 5.0 | 1.0 | 4.0 | 0.8 | 2.0 |
| | Na | 1.6 | 5.6 | 1.2 | 4.0 | 0.8 | 3.2 | 0.6 | 1.6 |
| 10 | K | 3.5 | 6.0 | 2.5 | 5.0 | 1.0 | 3.0 | 0.8 | 2.0 |
| | Na | 2.8 | 4.8 | 2.0 | 4.0 | 0.8 | 2.4 | 0.6 | 1.6 |
| 15 | K | 3.0 | 7.0 | 2.0 | 5.0 | 1.0 | 5.0 | 0.9 | 2.0 |
| | Na | 2.4 | 5.6 | 1.6 | 4.0 | 0.8 | 4.0 | 0.7 | 1.6 |

Allowing for the 0.8 differential between sodium azide and potassium azide, the $LC_0$ of chinook salmon treated with sodium azide is substantially greater than that of sockeye and steelhead (Tables 1 and 2). Thus, the selectivity and safety indices for chinook versus stickleback are correspondingly greater (Table 6).

Table 6.

Approximate selectivity and safety indices for the threespine stickleback and chinook salmon assayed in artesian well water.

| Tempera- ture, C. | Index | Elapsed time, hours | | | |
|---|---|---|---|---|---|
| | | 12 | 24 | 48 | 96 |
| 5 | Selectivity | 14 | 13 | 19 | 23 |
| | Safety | 2 | 2 | 3 | 6 |
| 10 | Selectivity | 9 | 12 | 27 | 27 |
| | Safety | 3 | 4 | 6 | 5 |
| 15 | Selectivity | 10 | 15 | 25 | 14 |
| | Safety | 5 | 5 | 4 | 5 |

These exploratory tests with few fish indicate that the toxicity of azides varies markedly with water quality. This could mean that the purer the water the less the cost of field applications of poison to control stickleback.

EXAMPLE 5 (Survival of game fish)

Experimental tests showed that sockeye that were exposed to sodium azide for 16 hours or less complete recovered from any ill effects of the toxicant as evidenced by 100 percent survival at the end of 20-day bioassays. Stickleback subjected to the same test conditions experienced almost 100% mortality.

EXAMPLE 6 (Deactivators for azides)

The inhibitory effect of compounds with calcium on the activity of azide was demonstrated in 12-hour bioassays with stickleback (mean length, 44 mm) at a temperature of 15 degrees Celsius.

Artesian well water and 10 fish (load: 0.7 g/l) were used for each experiment. The chemicals were assigned to five bioassay aquaria as indicated in Table 7.

Table 7.

The neutralizing effect of calcium chloride and calcium iodide mixed with 20 mg/l of potassium azide on the survival of the threespine stickleback in artesian well water.

| Aqua- rium | Chemical | Concen- tration mg/l | Equivalent weight | Survival Time/hours |
|---|---|---|---|---|
| 1 | Potassium azide | 20 | — | 2.3 |
| 2 | Potassium azide +calcium chloride | 20 14 | 1 1 | 7.4 |
| 3 | Potassium azide +calcium chloride | 20 28 | 1 2 | 8.4 |

Table 7.-continued

The neutralizing effect of calcium chloride and calcium iodide mixed with 20 mg/l of potassium azide on the survival of the threespine stickleback in artesian well water.

| Aqua- rium | Chemical | Concen- tration mg/l | Equivalent weight | Survival Time/hours |
|---|---|---|---|---|
| 4 | Potassium azide +calcium iodide | 20 36 | 1 1 | 11.3 |
| 5 | Potassium azide +calcium iodide | 20 72 | 1 2 | 11.3 |

Table 7 shows that halogenated compounds of calcium delayed mortality in stickleback that were exposed to excessive concentrations of azide. The table also indicates that calcium iodide neutralized azide more effectively than calcium chloride.

The addition of the calcium compounds to artesian well water extended the survival time of stickleback exposed to potassium azide significantly. The effect of adding 4 equivalent weights of the deactivator is not listed in Table 7 as the result was very similar to that for 2 equivalent weights. For both 2 and 4 equivalents 100% mortalities were obtained in 8.4 hours. Likewise, the effect of adding ½ equivalent weights of deactivator is not listed in Table 7 as the 100% mortality time was 3.0 hours and was not much more than the 2.3 hours of the control.

One equivalent weight of deactivator is almost as effective as two. One equivalent weight plus an excess (10 or 20% by weight) could be just as effective as two equivalents. The excess is probably necessary to neutralize any other interfering compounds in natural waters and ensure the completion of its neutralizing action on the azides. Water quality might greatly alter the effectiveness of the deactivator. This aspect we have not explored.

EXAMPLE 7 (Delayed application of deactivator)

Fingerling sockeye salmon in artesian water were exposed to a concentration of 5 mg/l of potassium azide for 24 hours at a temperature of 15 degrees Celsius. After 24 hours, 1, 2, 4 and 8 equivalent weights (3.5, 7.0, 14.0 and 28.0 mg/l) of calcium chloride were added and the effect on mortality was noted in 12-day bioassays.

Ten sockeye (length range, 55–93 mm) were assigned to each of four aquaria (load, 2.7 g/l) and concentrations of chemicals were added as indicated in Table 8. The time of mortality was noted.

Table 8.

The effect of calcium chloride on the survival time of sockeye salmon in artesian well water exposed 24 hours to 5 mg/l of potassium azide in 12-day bioassays.

| Calcium Chloride | | Survival time, |
|---|---|---|
| Concentration mg/l | Equivalent weight | hours |
| 3.5 | 1 | 90 |
| 7.0 | 2 | 112 |
| 14.0 | 4 | 148 |
| 28.0 | 8 | Did not die |

Table 8 shows that the addition of 1, 2, 4, and 8 equivalent weights of calcium chloride to a series of aquaria delayed the mortality of sockeye that had already been exposed to 5 mg/l of potassium azide for 24 hours. The addition of 8 equivalents of calcium chloride permitted the complete survival of all sockeye in the azide.

The toxicity of azide in standing water and the duration of its potency can be controlled by the addition of various amounts of calcium chloride, calcium iodide or stannous chloride. A deactivator in field applications of azide enhances the selective properties of azide and the survival of desirable fishes and other aquatic organisms.

Tests to date have shown that the death time for stickleback is about doubled if calcium chloride and potassium azide are added about simultaneously to the assay water. Also, the tests suggest that the death time of stickleback is not significantly shortened when the addition of deactivator is delayed longer than 4 hours.

We observed sockeye for a ten-day period. At a concentration of 5 mg/l of potassium azide regardless of when the deactivator was added, no sockeye in the series died in 6 days and only 40% of them died in 10 days. At a concentration of 7 mg/l of potassium azide and deactivator no salmon died in the series in 4 days and 84% of them died in 10 days.

For maximizing the kill of stickleback at 5 mg/l of potassium azide, a 2-hour delay in application of calcium chloride seems as long a time as necessary in artesian water. For water with different chemistry and for application of different concentrations of the azide the delay time of application of deactivator could vary. Applications of potassium azide at some concentration less than 5 mg/l with subsequent application of a deactivator would appear to have no lethal long term effects.

GENERAL DISCUSSION

The alkali salts of azide expressed in milligrams per liter have been used exclusively in the foregoing examples. Any compounds that contain the azide radical ($N_3$—) and dissociate or hydrolyse to form free azide radicals in water will be equally selective as the alkali salts of the azide. However, the toxicity of other azides that might be substituted would vary according to the equivalent weights of the azide compounds.

For example, when the active azide radical is applied in a field application at a concentration of 1.0 mg/l, the equivalent weight of sodium azide applied would be 65/42 or 1.55 mg/l; the equivalent weight of potassium azide applied would be 81/42 or 1.93 mg/l. Molecules with larger equivalent weights require correspondingly higher concentrations.

Azidotrimethylsilicane (mol. wt., 115) is an example of an organic compound containing the azide radical. To apply the active azide radical at a concentration of 1.0 mg/l, 2.7 mg/l of azidotrimethylsilicane would be required. We have made an exploratory test with azidotrimethylsilicane which verifies our contention that the azide radical ($N_3$—) in organic compounds are equally biologically active or potent and equally selective.

Sodium azide is probably the most economical, and a safe and easy compound to apply in field situations. For these reasons and for the practicality of easy referral to working concentrations of sodium azide, sodium azide rather than the azide radical is used as a standard for estimating toxicity values.

The 1974 Toxic Substances List published by the U.S. Department of Health, Education and Welfare gives the lowest published lethal dose of sodium azide. The $LDL_0$ for oral doses with rats is 46 mg of sodium azide for 2 kg of rat. It would be impossible for a bird or mammal to drink enough water when treated at 1 mg/l of azide for the azide to harm the animal. To drink a lethal dose, an animal would have to drink 46 times its weight in water. Nevertheless safety precautions should be taken when handling the chemical.

Additional tests have shown that sodium azide is not toxic to freshwater races of rainbow trout, cutthroat trout (*Salmo clarki*), bridgelip sucker (*Catastomus columbianus*), speckled dace (*Rhinichthys cataractae*), redside shiner (*Richardsonius balteatus*), and torrent sculpin (*Cottus rotheus*) at concentrations up to 1.5 mg/l in river water and 5.0 mg/l in artesian well water in 96-hour bioassays. These tests demonstrate that azides are not generally harmful to other species of fish but are selective only for stickleback.

The optimum range of concentration of azide varies with temperature, water quality, and species of compared fish. From the foregoing tables it can be seen that at any temperature from 5 to 15 degrees Celsius there is a range of concentrations in which the toxicant will achieve a 100 percent mortality of stickleback without any harmful effects on salmon or trout. It is preferable that a concentration within this range be chosen. However, conditions may warrant using more or less than the preferred amount.

For field applications the concentration of $NaN_3$ or $N_3$— would vary with water quality—mainly with regard to dissolved solid and hydrogen ion concentrations. Generally, treated areas would contain water low in dissolved solids and a pH of 7 to 7.5. The activity of the azide radical would then be essentially similar to that determined in our tests using river water. For the treatment of rivers and shorelines of lakes the concentrations of azide that would be used would be those that would kill stickleback in 12 to 24 hours. From our tests to date using natural river water, we can recommend 1.5 mg/l of $NaN_3$ or 1.0 mg/l of $N_3$— to be a safe and effective concentration to apply in the field under normal conditions (e.g. 20–50 mg/l of total dissolved solids, a pH in the range of 7.0 to 7.5, and at water temperatures of 10° to 15° C.).

According to our data using river water stickleback can be controlled with $NaN_3$ at concentrations-
- between 0.5 and 2.2 mg/l for sockeye at 15° C.
- between 0.5 and 3.0 mg/l for steelhead at 10° C.
- between 0.5 and 2.0 mg/l for steelhead at 15° C.
- between 0.5 and 4.0 mg/l for Kamloops at 15° C.
- between 0.5 and 5.0 mg/l for cutthroat at 15° C.
- and between 0.5 and 4.0 mg/l for brook trout at 10° C. and 15° C.

These values can be converted to mg/l of the azide radical by multiplying by 0.65. In general, the required practical concentration of the free azide radical in water ranges between 0.325 and 3.25 mg/l.

In combating the stickleback in accordance with this invention, it is desirable that azide be added to a stream so that concentrations will be substantially uniform throughout the water system. Thus, the natural flow and movement of the water and/or the method of application may serve to facilitate the dispersion and mixing and may reduce the amount of labor and equipment necessary for securing and maintaining the desired conditions.

The amount of azide required did not depend to any appreciable extent upon the size or weight of the fish treated but appears to be equally lethal to stickleback of all sizes.

The chemical literature indicates that azides can be decomposed by extracts from liver, kidney, potatoes, sugar beets and apples. Because of this and the results of degradation tests with a mud substrate which enhanced the survival of fish we assume that suspended organic materials or detritus on the bottom of treated waters would contribute to the degradation of low concentrations of azide appropriate to kill stickleback.

Published reports also have indicated that azides are decomposed by sunlight. This is substantiated by our experiments.

In treating a stream, pond or lake, azide may be added directly to the water in the form of a fine powder, with or without suitable wetting or conditioning agents, to facilitate dispersal and/or solution. Alternatively, the compound may be added in liquid form as solutions, suspensions, or emulsions. In general, aqueous solutions or dispersals are preferred because the application and mixing are more readily effected. The azide may be dissolved in water miscible solvents or it may be added in the form of a concentrated aqueous suspension. The azide suspension may be prepared from a solution of nonpolar solvents, or the like, as necessary to alter the density of the solution, to facilitate dispersion and mixing.

Depending on the species of desirable fish, and the temperature and chemistry of the water, optimum concentrations of azide that flush out or dilute within an appropriate time period may be used in any waters. Bodies of water that fit these requirements include streams, estuaries, tidal pools and the shorelines of lakes and the coastal areas of the ocean.

The alkali salts of azide do not seem to degrade very rapidly. The selectivity and safety indices of the azides are sufficient however, to allow its use in situations where it could become diluted rapidly with water when application ceases. Such situations could involve streams, tidepools, estuaries and the shoreline of lakes.

The use of a deactivator could greatly increase the size of the selectivity and safety indices of the azides.

Some of the favorable chemical qualities of the azides tested to date are as follows:

(1) They are non-chlorinated compounds;
(2) They are not organo-phosphates;
(3) They contain no heavy metal ions;
(4) They do not appear to irritate or repel fish in our test aquaria.

On the practical side for field applications, both sodium azide and calcium chloride should be relatively cheap and easily available, they are water soluble and can be transported as a dry powder. Neither should deteriorate with time.

Having described our invention, we claim:

1. A method of fish culture for control of the stickleback population in an aqueous habitat containing stickleback and at least one member selected from the group comprising sockeye salmon, chinook salmon, steelhead trout, rainbow trout, cutthroat trout, suckers, dace, shiners and sculpin, said method comprising:
   adding to the aqueous habitat a compound containing the azide radical and which dissociates or hydrolyzes to form a concentration of free azide radical in water from about 0.325 to 3.25 mg/l which is lethal to the stickleback, but not lethal to said selected members of said group.

2. A method of fish culture as set out in claim 1 wherein the compound is sodium azide.

3. A method of fish culture as set out in claim 1 wherein the compound is potassium azide.

4. A method of fish culture as set out in claim 1 wherein the compound is an organic compound containing the azide radical.

5. A method of fish culture as set out in claim 1 wherein the compound is azidotrimethyl-silicane.

6. A method of fish culture as set out in claim 1 further comprising the step of subsequently treating the aqueous habitat with a calcium compound which dissociates in water and decreases the toxic effects of the azide radical.

7. A method as set out in claim 6 wherein the calcium compound is calcium iodide.

8. A method as set out in claim 6 wherein the calcium compound is calcium chloride.

9. A method of fish culture as set out in claim 1 further comprising the step of subsequently treating the aqueous habitat with stannous chloride to decrease the toxic effects of the azide radical.

* * * * *